United States Patent [19]

Klaas

[11] Patent Number: 5,522,891
[45] Date of Patent: Jun. 4, 1996

[54] INTRAOCULAR LENS

[76] Inventor: Dieter W. Klaas, Bahnhofstrasse 5, 86316 Friedberg, Germany

[21] Appl. No.: 319,002

[22] Filed: Oct. 6, 1994

[30] Foreign Application Priority Data

Nov. 25, 1993 [DE] Germany ............... 43 40 205.4

[51] Int. Cl.$^6$ ............................................. A61F 2/16
[52] U.S. Cl. ............................................................. 623/6
[58] Field of Search ................................................. 623/6

[56] References Cited

U.S. PATENT DOCUMENTS

| 4,409,691 | 10/1983 | Levy . |
| 4,435,856 | 3/1984 | L'Esperance . |
| 4,512,040 | 4/1985 | McClure . |
| 4,816,031 | 3/1989 | Pfoff . |
| 4,888,016 | 12/1989 | Langerman ........................ 623/6 |
| 4,892,543 | 1/1990 | Turley . |
| 4,932,966 | 6/1990 | Christie et al. . |
| 5,275,624 | 1/1994 | Hara et al. ........................ 623/6 |

FOREIGN PATENT DOCUMENTS

| 0337390 | 4/1989 | European Pat. Off. . |
| 4038088 | 6/1992 | Germany ........................ 623/6 |
| 9305733 | 4/1993 | WIPO ........................... 623/6 |

*Primary Examiner*—Mary Beth Jones
*Attorney, Agent, or Firm*—Keck, Mahin & Cate

[57] ABSTRACT

An intraocular lens with an accommodation device which consists of a lens part 1, which can be shifted when the optical axis 2 is placed at an incline with respect to the force of gravitation, where the refractive power of the lens is increased by the shift of the lens part 1 when the optical axis is at an incline

10 Claims, 2 Drawing Sheets

INTRAOCULAR LENS

FIELD OF THE INVENTION

The invention relates to an intraocular lens with accommodation. The accommodation of the eye for far vision and near vision occurs in the intact natural lens by a change in the curvature of the lens. This results in a corresponding change in the refractive index of the lens. When the natural lens is replaced by an intraocular lens, it is known to provide zones in the intraocular lens which are intended for far vision and zones for close vision. In such intraocular lenses only a fraction of the incident light of the retina becomes available in each instance for far or near vision.

SUMMARY OF THE INVENTION

It is the purpose of the invention to create an intraocular lens of the type mentioned in the introduction, in which the entire amount of light is focused on the retina for far vision and near vision.

This task is solved according to the invention in that the accommodation device has a lens part which can be moved by the force of gravity when the optical axis is inclined with respect to the horizontal level and in that the lens refractive index of the intraocular lens is increased by the lens part which can be moved when the optical axis is put at an incline. In the horizontal position of the optical axis or of the eye, the eye assumes a position for far vision. The position of the parts located in the optical axis is such that the refractive index of the lens is adapted for far vision. When the optical axis is at a downward incline with respect to the horizontal for near vision, for example for reading, the lens part is moved in such a manner that the refractive index of the intraocular lens is increased accordingly.

This can be achieved if the lens part is located outside of the optical axis when the optical axis is in the horizontal position or it can be achieved by moving the lens part along the optical axis. For this purpose the lens part can have an increased refractive index compared to the lens parts which are in the horizontal optical axis, and it can be kept outside of the optical axis when the optical axis is in the horizontal position. The movable lens part can be made of a hard substance, for example a hydrogel, silicone, polymethylmethacrylate or another appropriate lens material. However, it is also possible to make the lens body fluid and to place it inside a second immiscible fluid. The lens body (solid or liquid) can be introduced into a lens chamber. This chamber can be provided on the front side of the lens body or it can surround the lens, forming a shell. Furthermore, the lens body can be shaped so that it has a higher density than the second fluid and it is located in a lower part of the hollow lens or the lens provided with the shell-shaped chamber, so that when the optical axis is horizontal the liquid lens part is outside of the optical axis and it is moved into the optical axis when the optical axis is inclined. It is also possible to use an air bubble which is surrounded by a fluid and which is located either in the optical axis of the eye or outside of the optical axis depending on the inclination of the head.

The lens body can be attached using a standard haptic system in the natural capsule bag of the eye. However it is also possible to implant the intraocular lens using an artificial capsule bag (DE 4,038,088 A1) in the eye. The lens body can be attached rigidly with the artificial capsule bag and it can be shaped in such a way that the lens part with the increased refractive index can only be moved into the optical axis when the latter is inclined with respect to the horizontal line.

However, it is also possible to move the lens part which is responsible for the accommodation along the optical axis of the interior of the capsule bag. The capsule bag can have an additional lens part which has a standard refractive index.

DETAILED DESCRIPTION OF THE DRAWINGS

Figure 1:
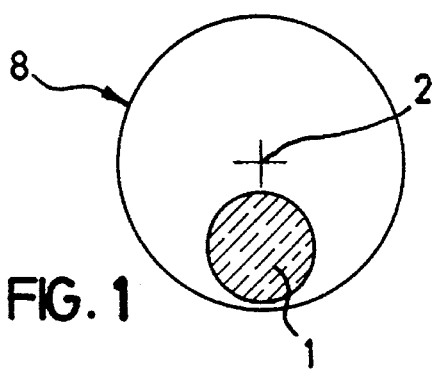
Figure 2:
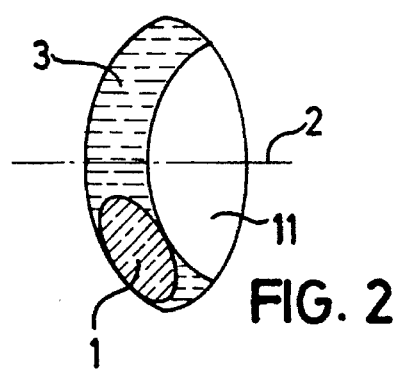
Figure 3:
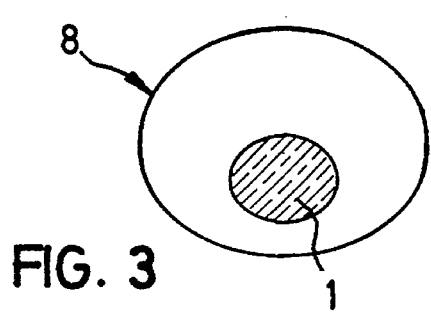
Figure 4:
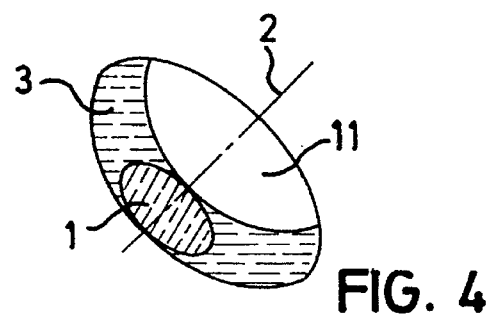
Figure 5:
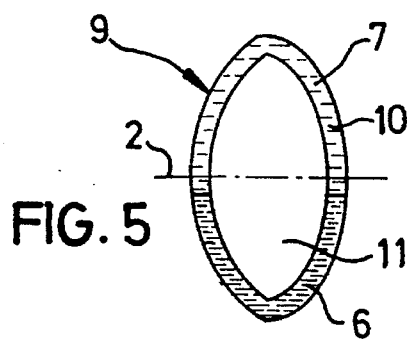
Figure 6:
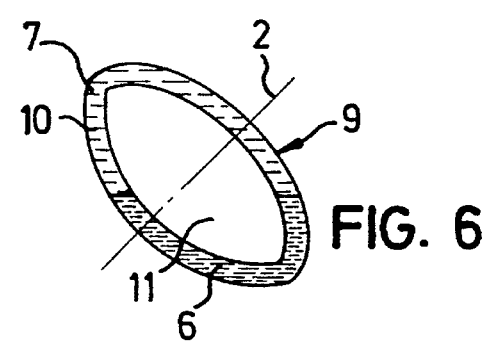
Figure 7:
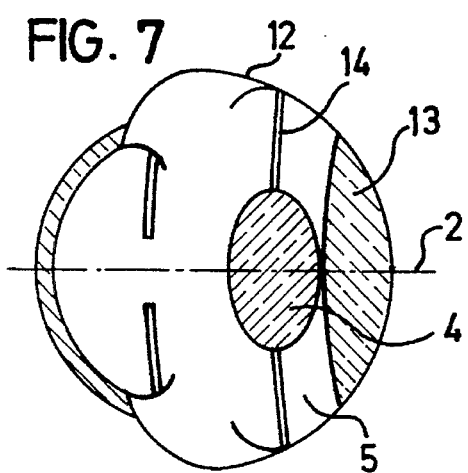
Figure 8:
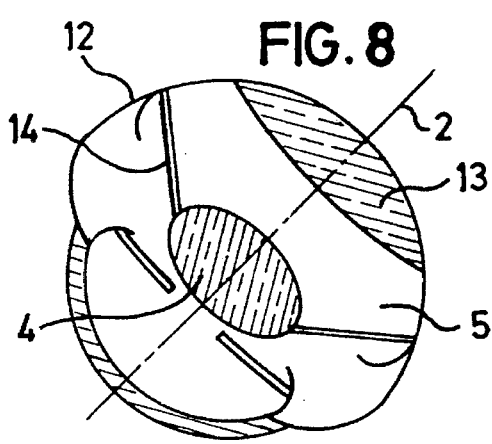
Figure 9:
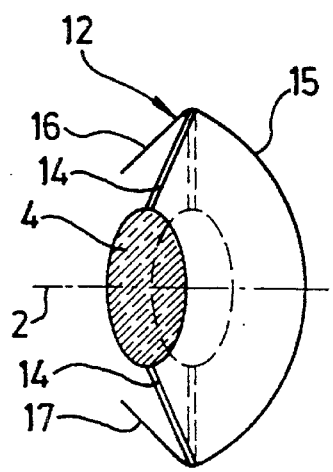
Figure 10:
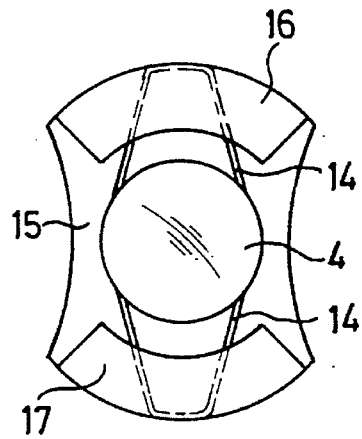
Figure 11:
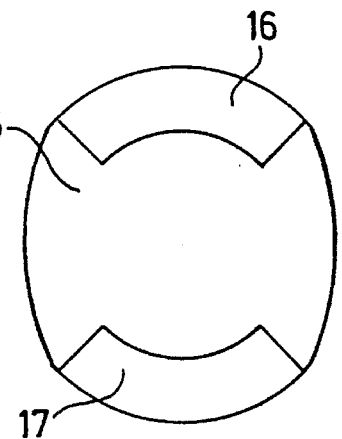
Figure 12:
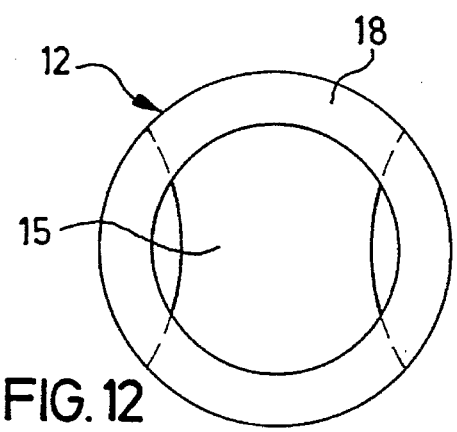
Figure 13:
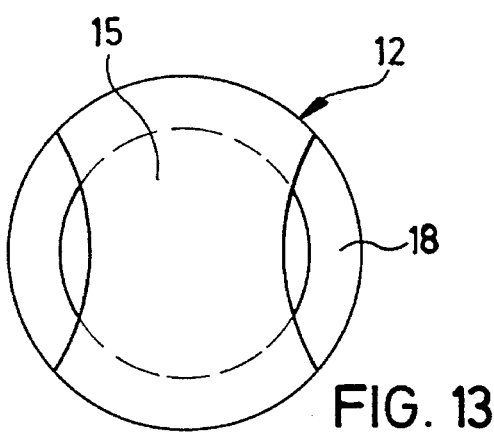
Figure 14:
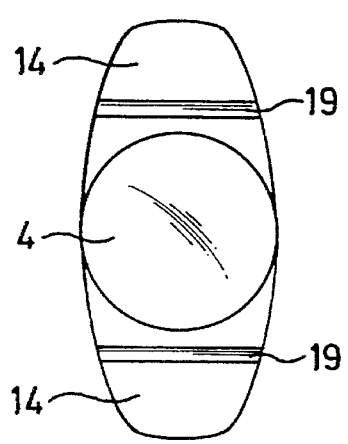
Figure 15:
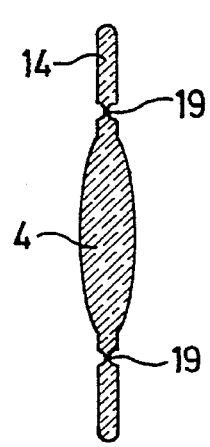
Figure 16:
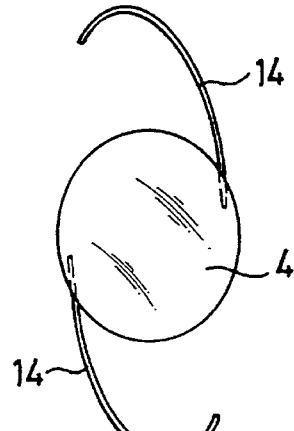

With reference to the figures the invention is explained further on the basis of embodiment examples. The figures show:

FIG. 1: a first embodiment example in frontal view with a horizontal optical axis;

FIG. 2: a lateral view of the embodiment example of FIG. 1;

FIG. 3: a frontal view of the embodiment example of FIGS. 1 and 2 with the optical axis at an incline with respect to the optical axis the horizontal level;

FIG. 4: lateral view of the arrangement shown in FIG. 3;

FIG. 5: a second embodiment example with a horizontal optical axis;

FIG. 6: the embodiment example shown in FIG. 5 with an inclined optical axis;

FIG. 7: a third embodiment example with a horizontal optical axis;

FIG. 8: the embodiment example of FIG. 7 with an optical axis with downward incline;

FIG. 9: a lateral view of a first embodiment example for the third embodiment example with artificial capsule bag;

FIG. 10: a frontal view of the embodiment form represented in FIG. 9;

FIG. 11: a frontal view of an additional embodiment form for the intraocular lens with artificial capsule bag;

FIG. 12: a third embodiment form for the embodiment example with the artificial capsule bag in a frontal view;

FIG. 13: a posterior view of the embodiment form of FIG. 12;

FIG. 14: a top view of an embodiment example for a movable lens part;

FIG. 15: a lateral view of the embodiment example represented in FIG. 14;

FIG. 16: an additional embodiment example of a movable lens part.

DETAILED DESCRIPTION OF THE PREFERRED EMBODIMENTS

The embodiment example represented in FIG. 1 shows a lens body 8 in an intraocular lens. This lens body can also be provided in the usual manner with a haptic system, not represented in detail, by means of which it is attached in the eye in the implanted state. The lens body 8 is fitted with a chamber 3. A lens part 1 is located in the chamber 3, which has a higher specific gravity than the medium, for example, a fluid which fills the remaining portion of the chamber 3. The lens part 1 has a higher refractive index than caused by the lens parts which are located in the horizontal arrangement of the optical axis 2 (arrangement of FIGS. 1 and 2). In the represented embodiment example with horizontal optical axis, the medium which fills the chamber 3, for example a transparent fluid, and a lens core 11 are located in the optical axis. In this arrangement the intraocular lens is adapted for far vision.

The lens part 1 can be made of a hard substance, for example, a conventional lens material such as PMMA, a hydrogel or silicon or a similar material. The fluid which fills the remainder of the chamber 3 can be silicone oil.

If, as indicated in FIG. 3 and 4, the optical axis is at a downward incline with respect to the horizontal line, the intraocular lens is adapted for near vision. Because of the force of gravity, the lens part 1 inside the chamber 3 moves so that it ends up in the inclined optical axis 2. As a result, the refractive index of the lens is increased for near vision. When the head is raised the lens part 1 again returns to the position illustrated in FIGS. 1 and 2.

The lens part 1 can also be made of a transparent fluid which is immiscible with the other fluid which fills the remaining portion of the chamber 3.

In the embodiment example represented in FIGS. 5 and 6, the lens core 11 is surrounded by a chamber 7 in the form of a shell. The chamber 7 can surround and hold the entire lens core 1 [sic; 11], but it can also surround and hold a middle area of the lens body or lens core 11, on the front and back sides and in the equatorial area, as is the case in chamber 3 of the embodiment examples of FIGS. 1 to 4. In the horizontal position of the optical axis 2, shown in FIG. 5, the lens is set for far vision. A fluid 6, which has a higher refractive index, is located outside of the optical axis 2, in the lower part of the shell-shaped chamber 7. Naturally it is also possible to fill the entire space of the lower lens part with the fluid 6, and the upper part of the lens body 9 with the second fluid, which has a lower refractive index than fluid 6. The two fluids 6 and 10 are immiscible. In the horizontal position of the optical axis 2 (FIG. 5), only the fluid 10 and the core 11 are in the optical axis. When the optical axis is inclined (FIG. 6), the fluid 6 moves in the optical axis and thus increases the refractive index of the lens for far vision.

In the embodiment example illustrated in FIGS. 7 and 8 a lens part 4 moves along the optical axis 2 in a schematically represented artificial capsule bag 12. The artificial capsule sac 12 can be formed as described in DE 4,038,088 A1. The artificial capsule bag 12 guarantees that a space is created for shifting the lens part 4 along the optical axis 2. The artificial capsule bag prevents the occurrence of shrinkage of the natural capsule bag, from which the natural eye lens has been removed. The natural capsule, in its entirety or at least in part, is maintained by the artificial capsule bag 12 in a shape which is such that it guarantees the required shift of the lens part 4 along the optical axis 2. The capsule bag 12 can be formed so that a maximum shift of 4-5 mm of the lens part 4 can take place in the space 5 created by the capsule bag 12. The lens part 4 is held and guided by means of an appropriate haptic system which permits shifting along the optical axis 2 on the basis of the force of the weight of lens part 4. To simplify the implantation the capsule bag can be made of a foldable material such as, for example, silicone rubber.

In the horizontal position of the optical axis 2, represented in FIG. 7, the lens part 4 is located in a posterior position within the chamber 5. In the position with downward slant of the optical axis 2, as illustrated in FIG. 8, the lens part 4 is shifted to the front in chamber 5 so that an accommodation for near vision is achieved. In this process, the haptic system 14, by means of which the lens part 4 is set in the artificial capsule bag 12, is expanded elastically. When the optical axis 2 is again in a horizontal position at a corresponding inclination of the head (FIG. 7), the lens part 4 is again moved back to the position illustrated in FIG. 7 as a result of the elasticity of the haptic system 14 so that the lens is adapted to far vision.

In the capsule bag 12, a rigidly attached additional lens part 13 can be provided. This additional lens part 13 can have a standard refractive index, for example minus 10 diopters. In that case it is preferred that the movable lens part 4 has a value of 30 diopters. If the lens part 4 is moved by 2.5 mm for example, the refractive index can be changed by 3.5 diopters.

FIGS. 9 to 13 are additional embodiment forms of the schematically represented artificial capsule bag 12 of FIGS. 7 and 8.

In the embodiment form of FIGS. 9 and 10 the capsule bag has a posterior wall section 15 which deviates from the shape of a circle. The artificial capsule interior only has a circular section in the area where the haptic system 14 is supported by the interior of the artificial capsule bag 12. In the illustrated example, these circular sections are in the top and bottom. In the lateral areas the posterior wall section 15 has recesses. The backside of the natural capsule bag is supported completely or partially by the posterior wall section 15, in such a way that the necessary ability of the lens part 4 to move along optical axis 2 is guaranteed, so that the desired accommodation can be achieved.

In order to keep the frontal part of the natural capsule at a distance from its backside, frontal capsule parts 16 and 17 in the form of circular ring segments are provided in the artificial capsule bag 12. Here, too, it is guaranteed that sufficient room is provided for an unimpeded accommodative movement of the lens part 4.

The embodiment form represented in FIG. 11 also contains the frontal capsule parts 16 and 17 in the form of circular ring segments. The posterior capsule part 15 also deviates from the circular shape, and, in contrast to the lateral recesses, it has slightly arched recesses in the lateral parts.

In the embodiment form represented in FIGS. 12 and 13, a posterior wall part 15 with a shape which differs from the circular form is provided, which has lateral recesses as the embodiment form of FIGS. 9 and 10. However, to fix the distance between the entire area of the frontal natural capsule and the posterior capsule part, the frontal capsule part 18 of the artificial capsule bag 12 is in the form of a ring.

In the embodiment examples of FIGS. 7 to 13 the lens part 4 can be moved along the optical axis 2 for the accommodative movement. This is guaranteed by the articulated design of the haptic system 14. The haptic system 14 can be supported with articulations on the interior side of the artificial capsule bag 12 and it can also allow articulated movement at the places of connection to the lens part 4. In addition, the material of the haptic system 14 is elastic to guarantee the required movement.

The material of the lens part 4 has a higher specific gravity than the aqueous humor. The specific gravity is preferably 1.3 to 2.0. This guarantees that the lens part 4 which is surrounded in the implanted state by the aqueous humor, performs the desired accommodative movement along the optical axis 2. As already explained, the artificial capsule bag 12 guarantees that the movement in the eye takes place unimpeded by natural components of the eye.

FIGS. 14 to 16 represent embodiment forms for movable lens parts 4. In the embodiment form represented in FIGS. 14 and 15 two flap-shaped haptic parts are provided. One or both haptic parts 14 can have a weakened section 19 over their entire width. As a result of the weakened section 19 the ability of the lens part 4 to move is guaranteed.

However, the haptic system 14 can also be constructed in the standard manner in the form of threads, as represented in FIG. 16. In FIGS. 7 and 8, the schematically represented ability of the lens part 4 to move in the artificial capsule bag 12 is guaranteed because of the elasticity of the thread 14.

I claim:

1. An intraocular lens including a device for accommodation, for implanting in an eye, comprising:

an artificial bag which prevents shrinkage of a natural capsule bag of the eye for implanting in the natural capsule bag of the eye;

a lens part suspended in the artificial bag by a haptic system, the lens part being movably guided along its optical axis by elasticity of the haptic system;

wherein when the optical axis of the lens part is slanted downward from a horizontal level, the haptic system is elastically expanded and the lens part is shifted by force of gravity along the optical axis to increase the refractive index of the intraocular lens and when the optical axis is again in a horizontal position the lens part is moved back to an initial position thereof by the elasticity of the haptic system.

2. Intraocular lens according to claim 1, wherein the lens part (4) is held by means of an elastic haptic system (14) in the artificial capsule bag (12).

3. Intraocular lens according to claim 1, wherein the artificial capsule bag (12) has a posterior wall part (15) by means of which a backside of the natural capsule bag can be supported at least partially.

4. Intraocular lens according to claim 3, wherein the artificial capsule bag (12) comprises a frontal capsule part (16,17,18) adapted for spacing a frontal natural capsule part away from the backside of the natural capsule bag.

5. Intraocular lens according to claim 4, wherein the frontal capsule part (16,17) is constructed in several parts.

6. Intraocular lens according to claim 4, wherein the frontal capsule part (18) is constructed as a ring.

7. Intraocular lens according to claim 1, wherein the artificial capsule bag (12) has a standard refractive index.

8. Intraocular lens according to claim 7, wherein the standard refractive index of the artificial capsule bag (12) is formed by an additional lens part (13) which is rigidly connected to the artificial capsule bag (12).

9. Intraocular lens according to claim 1, wherein the lens part (4) comprises a material which has a higher specific gravity than aqueous humor.

10. Intraocular lens according to claim 1, wherein the artificial capsule bag (12) is constructed in a foldable way.

* * * * *